US006610248B1

(12) United States Patent
Lichtenberg et al.

(10) Patent No.: US 6,610,248 B1
(45) Date of Patent: Aug. 26, 2003

(54) DISINFECTANTS

(75) Inventors: Florian Lichtenberg, Grenzach-Wyhlen (DE); Michael Lützeler, Grenzach-Whylen (DE); Volker Ranft, Murg (DE)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/926,819

(22) PCT Filed: Jun. 23, 2000

(86) PCT No.: PCT/EP00/05871

§ 371 (c)(1),
(2), (4) Date: Dec. 26, 2001

(87) PCT Pub. No.: WO01/00024

PCT Pub. Date: Jan. 4, 2001

(30) Foreign Application Priority Data

Jun. 25, 1999 (EP) ............................................. 99112262

(51) Int. Cl.⁷ ................................................. A61L 2/00
(52) U.S. Cl. .......................... 422/28; 210/764; 514/663
(58) Field of Search ............................ 422/28; 514/663, 514/671, 673; 424/405; 210/764

(56) References Cited

U.S. PATENT DOCUMENTS

| 3,912,816 A | 10/1975 | Hoffman et al. |
| 4,416,808 A | 11/1983 | Blaschke et al. |
| 5,760,091 A | 6/1998 | Wakao et al. |

FOREIGN PATENT DOCUMENTS

| EP | 0080137 | 6/1983 |
| EP | 0343605 | 11/1989 |
| GB | 1300694 | 12/1972 |

*Primary Examiner*—Elizabeth McKane
(74) *Attorney, Agent, or Firm*—Fisher, Christen & Sabol

(57) ABSTRACT

Disinfectants having N,N-bis(3-aminopropyl)octlyamine as the active substance. The disinfectants are characterized by good activity also against mycobacteria, low efficiency loss under protein load and little foaming. The disinfectants are particularly useful for disinfecting surfaces, containers and pipelines, for instance, in the food industry, and for disinfecting instruments, especially automatic instrument disinfection at low temperatures.

26 Claims, No Drawings

DISINFECTANTS

This is a 371 of PCT/EP00/05871, filed on Jun. 23, 2000, that has priority benefit of European Patent Application 99112262.3, filed on Jun. 25, 1999.

The invention relates to disinfectants based on N,N-bis(3-aminopropyl)octylamine of the formula

$n\text{-}C_8H_{17}\text{---}N\ [(CH_2)_3\text{---}NH_2]_2.$

It is known that N,N-bis(3-aminopropyl)dodecylamine (tradename LONZABAC®12) has good microbicidal activity and is also active in particular against mycobacteria. This compound is also distinguished by good compatibility with surfactants, and low corrosivity. However, as with many other microbicidal active substances, the activity in the presence of proteins and/or hard water markedly decreases and turbidity or even precipitates occur. In addition, formulations containing N,N-bis(3-aminopropyl)dodecylamine have a strong foaming tendency, which makes them unsuitable for some applications or requires special measures.

It is therefore an object of the present invention to provide disinfectants which, for a comparable spectrum of activity, have low foaming and low loss of activity in the presence of the proteins.

According to the invention, this object is achieved by the use of N,N-bis(3-aminopropyl)octylamine as a biocide and as the disinfectant of the invention.

It has surprisingly been found that the compound N,N-bis(3-aminopropyl)octylamine (EP-A-0 080 137), which is known as an intermediate in the synthesis of surfactants, has good antibacterial activity, in particular against mycobacteria also, which remains virtually unchanged even in the presence of proteins. In addition, this compound has low foaming tendency.

The inventive disinfectants expediently comprises from 0.1 to 30.0% of N,N-bis(3-aminopropyl)octylamine and at lease on of the auxiliary which is selected form the group consisting of solvents, surfactants, complexing agents, colorants, fragrances, acids or bases for setting pH, inorganic and organic salts (for example borates, silicates, carbonates, rhodanides).

Preferably, the inventive disinfectants comprise water as solvent.

In a preferred embodiment, the inventive disinfectants comprise, as additional active compound, an amine oxide. Suitable amine oxides are, for example, N,N-di-$C_{1-4}$-alkyl-$C_{6-22}$-alkylamine oxides, preferably N,N-dimethyl-$C_{8-18}$-alkylamine oxides. Amine oxides of this type are obtainable, for example, under the name BARLOX® from Lonza AG.

The inventive disinfectants are suitable, in particular, for use in CIP systems (cleaning in place), for disinfecting containers, surfaces and pipelines in the food industry, for preventing microbial contamination of closed water circuits, for example in the paper industry or in the cooling towers, and for disinfecting surfaces in hospitals, for disinfecting instruments, for disinfecting recirculating toilets, for water treatment (for example in swimming pools) and for wood preservation.

A particularly preferred use is automatic disinfection of instruments at temperatures of less than 60° C., in particular in automatic apparatuses, for example for disinfecting endoscopes.

The examples below illustrate the inventive procedure, without a limitation to be seen therein. Unless otherwise stated, all percentages are percentages by weight.

EXAMPLE 1/COMPARATIVE EXAMPLE 1

Determination of Foaming

Method:

A 250 ml mixing cylinder was filled with 100 ml of solution. After any foam formed in the course of this had disappeared, the sealed cylinder was shaken vigorously vertically for 15 s (approximately 15×) and then placed on a flat support. The volume of the resultant foam was read off at regular time intervals.

Results:

With a solution of 250 ppm of N,N-bis(3-aminopropyl)octylamine in demineralized water at 20° C. after 10 s 20 ml of foam was observed, the volume of which decreased to half that in a further 10 s. After 60 s the foam had virtually completely disappeared. As a comparison, the same test was carried out using N,N-bis(3-aminopropyl)dodecylamine. The foam volume after 10 s was 140 ml and after 60 s was still 120 ml.

EXAMPLE 2/COMPARATIVE EXAMPLE 2

Quantitative Suspension Test (EN 1276)

As specified by standard EN 1276, the efficacy of N,N-bis(3-aminopropyl)octylamine (according to the invention) and N,N-bis (3-aminopropyl)dodecylamine (comparison) was determined in the presence of albumin for various test microorganisms. The results are summarized in Table 1 below.

| | |
|---|---|
| Contact time: | 5 min |
| Water hardness (as $CaCO_3$): | 300 mg/kg |
| Temperature: | 20° C. |
| Log. reduction: | >5 |

TABLE 1

| | 0.03% albumin | | 0.3% albumin | |
|---|---|---|---|---|
| Test micro-organism | According to the invention | Comparison | According to the invention | Comparison |
| *Pseudomonas aeruginosa* ATCC 15442 | 0.05% | 0.025% | 0.10% | 0.50% |
| *Staphylococcus aureus* ATCC 6538 | 0.10% | 0.05% | 0.10% | 0.10% |
| *Escherichia coli* ATCC 10536 | 0.05% | 0.025% | 0.05% | 0.025% |
| *Enterococcus hirae* ATCC 8043 | 0.10% | 0.05% | 0.05% | 0.05% |

A significantly smaller fall in activity in the presence of 0.3% albumin was found, in particular towards P. aeruginosa.

EXAMPLE 3/COMPARISON EXAMPLE 3

Formulation Containing Nonionic Surfactant

A liquid formulation was prepared from:

| | |
|---|---|
| 10.0% | N,N-bis(3-aminopropyl)octylamine |
| 2.5% | Trilon ® A (nitrilotriacetic acid, sodium salt; 40% strength aqueous solution) |
| 10.0% | Genapol ® PF 10 (ethylene oxide-propylene oxide) block polymer containing approximately 10% ethylene oxide |
| 77.5% | water |

A formulation containing the same amount of N,N-bis-(3-aminopropyl)dodecylamine instead of N,N-bis(3-amino-propyl)octylamine, otherwise having the same composition, served as comparison. Foaming was determined for both formulations by the method described in Example 1. The foam volume for the inventive formulation was, after 10 s, 50 ml, and, after 60 s, 30 ml. In the case of the comparison formulation, the foam volume after 10 s was 150 ml and after 60 s was still 100 ml.

EXAMPLE 4

Formulation Containing Anionic Surfactant

A liquid formulation was prepared from

| | |
|---|---|
| 10.0% | N,N-bis(3-aminopropyl)octylamine |
| 2.5% | Trilon ® A (40% strength aqueous solution) |
| 10.0% | Genapol ® LRO ($C_{12}/C_{14}$-alkyl diglycol ether sulfate, Na salt; surfactant substance approximately 27%) |
| 77.5% | water. |

EXAMPLE 5

Formulation Containing Cationic Surfactant

A liquid formulation was prepared from

| | |
|---|---|
| 10.0% | N,N-bis(3-aminopropyl)octylamine |
| 2.5% | Trilon ® A (40% strength aqueous solution) |
| 10.0% | BARDAC ® 22-40 (didecyldimethylammonium chloride, 40% strength aqueous solution) |
| 77.5% | water. |

EXAMPLE 6

Formulation Containing Amphoteric Surfactant

A liquid formulation was prepared from

| | |
|---|---|
| 10.0% | N,N-bis(3-aminopropyl)octylamine |
| 2.5% | Trilon ® A (40% strength aqueous solution) |
| 10.0% | Amphoterge ® K-2 (cocoimidazoline dicarboxylate; Lonza AG) |
| 77.5% | water. |

EXAMPLE 7

Formulation Containing Amine Oxide

A liquid formulation was prepared from

| | |
|---|---|
| 10.0% | N,N-bis (3-aminopropyl)octylamine |
| 2.5% | Trilon ® A (40 strength aqueous solution) |
| 10.0% | BARLOXr 12 (lauryl dimethyl amine oxide) |
| 77.5% | water. |

EXAMPLE 8

Quantitative Suspension Test Using *Mycobacterium terrae*

Using the method described in *Hygiene & Medizin* 1997, 22, pp. 278–283, the activity of N,N-bis(3-amino-propyl)octylamine against *Mycobacterium terrae* ATCC 15755 was determined under differing organic loads. The concentration of active compound was in each case 0.3%, the temperature 20° C. and the contact time 15 min. The common logarithmic reduction in bacterial count was determined each time. The results were as follows:

| Load | Log reduction |
|---|---|
| None | 4.33 |
| 0.3% albumin | 4.09 |
| 0.5% sheep's blood | 4.48 |

EXAMPLE 9

Formulation Containing Amine Oxide/Quantitative Suspension Test Using *M. terrae*

A liquid formulation (concentrate) was prepared from

| | |
|---|---|
| 10.0% | N,N-bis(3-aminopropyl)octylamine |
| 4.5% | Trilon ® BS (ethylenediaminetetraacetic acid, solid) |
| 2.0% | BARLOX ® 12i(isododecyldimethylamine oxide) |
| 83.5% | Water |

The formulation was a clear and storage-stable yellow solution having a pH of 9.6. A 1% strength dilution in the mains water had a pH of 9.2 and, in the test performed by the method described in Example 1, after 20 s a foam volume of 0 ml was found. The bactericidal activity of the formulation was determined in the DGHM suspension test using *Mycobacterium terrae* ATCC 15755 as test microorganism at 38° C. The bacterial content of the initial suspension was $10^{10.21}$/ml. The results of the test are summarized in table 2 below. The data reported in each case are the concentration (dilution) of the formulation in (concentrate: 100%) and the common logarithmic reduction factors in bacterial counts found after in each case 2½, 5 and 10 minutes of exposure time and the common logarithmic values of absolute bacterial counts in control samples (without disinfectant) at 20° C. and 38° C.

TABLE 2

| c[%] | 2½ min | 5 min | 10 min |
|---|---|---|---|
| 1.0% | 3.81 | 4.31 | ≧6.06 |
| 0.5% | 2.95 | 3.30 | 4.23 |
| 0.1% | 0.78 | 1.07 | 1.34 |
| Control (20° C.) | 7.24 | 7.10 | 7.06 |
| Control (38° C.) | 7.16 | 7.01 | 7.00 |

What is claimed is:

1. A process comprising contacting an object with N,N-bis(3-aminopropyl)octylamine that has biocidal activity.

2. A process comprising treating water with N,N-bis(3-aminopropyl)octylamine that has biocidal activity.

3. A disinfectant comprising from 0.1 percent to 30 percent of N,N-bis(3-aminopropyl)octylamine and at least one auxiliary selected from the group consisting of solvents, surfactants, complexing agents, colorants, fragrances, acids, bases, inorganic salts and organic salts.

4. The disinfectant as claimed in claim 3, where water is present as the solvent.

5. A process comprising disinfecting at least one container in the food industry by means of the disinfectant of claim 4.

6. A process comprising disinfecting at least one pipeline in the food industry by means of the disinfectant of claim 4.

7. A process comprising disinfecting at least one instrument by means of the disinfectant of claim 4.

8. The process as claimed in claim 7, wherein the disinfection is carried out at a temperature below 60° C.

9. The process as claimed in claim 8, wherein the disinfection is carried out in an automatic apparatus.

10. The disinfectant as claimed in claim 4, wherein said disinfectant also contains at least one amine oxide as an additional active compound.

11. The disinfectant as claimed in claim 10, wherein the amine oxide is an N,N-dimethyl-$C_{8-18}$-alkylamine oxide.

12. A process comprising disinfecting at least one container in the food industry by means of the disinfectant of claim 10.

13. A process comprising disinfecting at least one pipeline in the food industry by means of the disinfectant of claim 10.

14. The disinfectant as claimed in claim 3, wherein said disinfectant also contains at least one amine oxide as an additional active compound.

15. A process comprising disinfecting at least one container in the food industry by means of the disinfectant of claim 3.

16. A process comprising disinfecting at least one pipeline in the food industry by means of the disinfectant of claim 3.

17. A process comprising disinfecting at least one instrument by means of the disinfectant of claim 3.

18. The process as claimed in claim 17, wherein the disinfection is carried out at a temperature below 60° C.

19. The process as claimed in claim 18, wherein the disinfection is carried out in an automatic apparatus.

20. A process comprising disinfecting at least one instrument using the disinfectant of claim 10.

21. The process as claimed in claim 20, wherein the disinfection is carried out at a temperature below 60° C.

22. The process as claimed in claim 21, wherein the disinfection is carried out in an automatic apparatus.

23. A disinfectant comprising from 0.1 percent to 30 percent of N,N-bis(3-aminopropyl)octylamine, at least one amine oxide as an additional active compound, and at least one auxiliary selected from the group consisting of solvents, surfactants, complexing agents, colorants, fragrances, acids, bases, inorganic salts and organic salts.

24. The disinfectants as claimed in claim 23, wherein the amine oxide is an N,N-dimethyl-$C_{8-18}$-alkylamine oxide.

25. The disinfectant as claimed in claim 23, where water is present as the solvent.

26. The disinfectant as claimed in claim 25, wherein the amine oxide is an N,N-dimethyl-$C_{8-18}$-alkylamine oxide.

* * * * *